(12) United States Patent
Ueda

(10) Patent No.: US 8,969,551 B2
(45) Date of Patent: Mar. 3, 2015

(54) MORPHOLINO NUCLEIC ACID DERIVATIVES

(75) Inventor: Toshihiro Ueda, Ibaraki (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 201 days.

(21) Appl. No.: 13/876,194

(22) PCT Filed: Sep. 29, 2011

(86) PCT No.: PCT/JP2011/072407
§ 371 (c)(1),
(2), (4) Date: Mar. 27, 2013

(87) PCT Pub. No.: WO2012/043730
PCT Pub. Date: Apr. 5, 2012

(65) Prior Publication Data
US 2013/0197220 A1    Aug. 1, 2013

(30) Foreign Application Priority Data

Sep. 30, 2010 (JP) .................. 2010-220865

(51) Int. Cl.
C07D 413/04 (2006.01)
C07D 473/18 (2006.01)
C07F 9/6558 (2006.01)
C07F 9/6561 (2006.01)

(52) U.S. Cl.
CPC .......... *C07D 473/18* (2013.01); *C07F 9/65583* (2013.01); *C07F 9/65616* (2013.01)
USPC ....................................................... 544/118

(58) Field of Classification Search
USPC ....................................................... 544/118
See application file for complete search history.

(56) References Cited

U.S. PATENT DOCUMENTS 7,943,762 B2 *  5/2011  Weller et al. .................... 536/31

FOREIGN PATENT DOCUMENTS

JP    2005-255530    9/2005
WO    2009/064471 A1    5/2009

OTHER PUBLICATIONS

B.L. Gaffney and R.A. Jones, "A New Strategy for the Protection of Deoxyguanosine During Oligonucleotide Synthesis," Tetrahedron Letters, vol. 23, No. 22, pp. 2257-2260 (1982), Great Britain, Pergamon Press Ltd.
Michinori Kadokura, Takeshi Wada, Kohji Seio, and Mitsuo Sekine, "Synthesis of 4-Thiouridine, 6-Thioinosine, and 6-Thioguanosine 3',5'-O-Bisphosphates as Donor Molecules for RNA Ligation and Their Application to the Synthesis of Photoactivatable TMG-Capped U1 snRNA Fragments," J. Org. Chem., vol. 65, No. 17, pp. 5104-5113 (2000), American Chemical Society.

* cited by examiner

*Primary Examiner* — Rebecca Anderson
*Assistant Examiner* — Karen Cheng

(57) ABSTRACT

The present invention provides a useful morpholino nucleic acid derivative for synthesizing a morpholino nucleic acid oligomer. The present invention provides a compound represented by the following general formula (1) or a salt thereof.

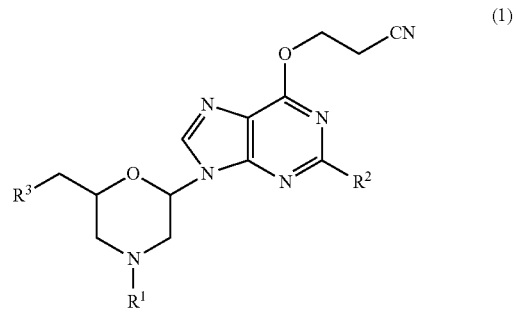

Here, $R^1$ represents hydrogen, trityl and so on.
$R^2$ represents an amide or an imine.
$R^3$ represents a hydroxy group which may be protected by trialkylsilyl and so on, or a group represented by the following general formula (5):

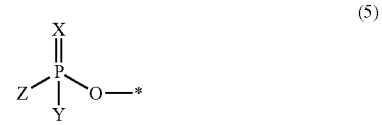

(wherein X represents O or S, Y represents dialkylamino or alkoxy, and Z represents chlorine).

16 Claims, 3 Drawing Sheets

MORPHOLINO NUCLEIC ACID DERIVATIVES

CROSS-REFERENCE TO RELATED APPLICATIONS

This patent application is a U.S. national stage entry under 35 U.S.C. §371 of International Patent Application No. PCT/JP2011/072407 filed on Sep. 29, 2011, which claims the benefit of foreign priority to Japanese Patent Application No. JP 2010-220865 filed on Sep. 30, 2010. The International Application was published in Japanese on Apr. 5, 2012, as International Publication No. WO 2012/043730 A1 under PCT Article 21(2).

FIELD OF THE INVENTION

The present invention relates to a novel morpholino nucleic acid derivative.

BACKGROUND OF THE INVENTION

A morpholino nucleic acid monomer whose base moiety is guanine (hereinafter referred to as a "G monomer") has an oxygen atom bound to the carbon atom in the 6-position of the guanine. Accordingly, when a morpholino nucleic acid oligomer is synthesized using a G monomer whose hydroxy group in the 6-position of the guanine is not protected, a side reaction occurs. For example, in a condensation process, the hydroxy group in the 6-position of the guanine may react with the activated site of other morpholino nucleic acid monomer to form a phosphorylated form, which may then react with ammonia used in a deprotection process, resulting in a conversion from the guanine to a diaminopurine. Such a side reaction serves as a substantial cause of a reduction in the synthesis yield of an intended substance.

For the purpose of suppressing the aforementioned side reaction, AVI BioPharma Inc. reported a G monomer whose hydroxy group in the 6-position of the guanine is protected by a pivaloyloxybenxyl group (POB group) (for example, see WO2009/064471 A1). Nevertheless, the POB group is converted during the deprotection process into 4-methylenecyclohexa-2,5-dienone, which is added to an NH moiety of the morpholine in the morpholino nucleic acid oligomer to form a by-product.

In addition, WO2009/064471 A1 includes a description of other protecting groups for the hydroxy group in the 6-position of the guanine. Such other protecting groups disclosed in WO2009/064471 A1 include, for example, 4-nitrophenethyl, phenylsulfonylethyl and methylsulfonylethyl. These protecting groups, however, undergo conversion during the deprotection process to reactive species such as 4-nitrostyrene, which is added to an NH moiety of the morpholine in the morpholino nucleic acid oligomer to form a by-product. While a silyl-type protecting group such as t-butyldimethylsilyl is also known, it has been reported to undergo a side reaction similar to that of the G monomer whose hydroxy group in the 6-position of the guanine is not protected, since it is not stable and tends to be cleaved easily under a morpholino nucleic acid oligomer synthesis condition. Furthermore, a phenyl ether-type protecting group and a carbamate-type protecting group are also known, but it is reported about these protecting groups that a detachment of the protecting group is imperfect in the deprotection process or that condensation efficiency turns worse in the condensation process.

BRIEF SUMMARY OF THE INVENTION

A main object of the invention is to provide a novel morpholino nucleic acid derivative for synthesizing a morpholino nucleic acid oligomer efficiently and a starting material for this derivative.

Applicants discovered that a compound represented by the following general formula (1) (hereinafter referred to as a "compound of the invention") or a salt thereof is useful as a starting material for synthesis of a morpholino nucleic acid oligomer or a starting material for obtaining such a starting material for synthesis, thus establishing the present invention.

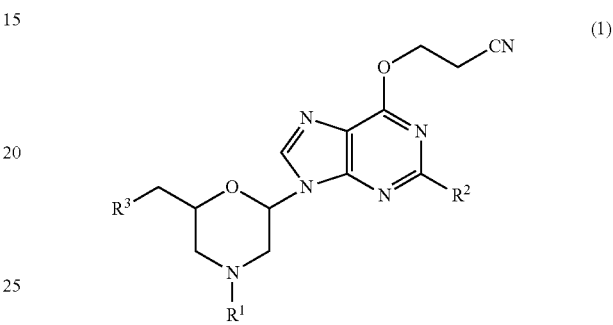

(1)

wherein $R^1$ represents hydrogen or a group represented by the following general formula (2).

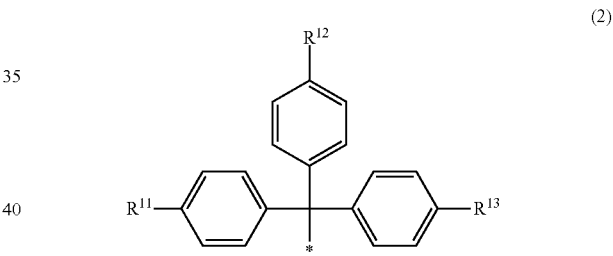

(2)

wherein * represents the binding position. $R^{11}$, $R^{12}$, and $R^{13}$ are the same or different and each represents hydrogen, alkyl or alkoxy.

$R^2$ represents a group represented by the following general formula (3) or (4).

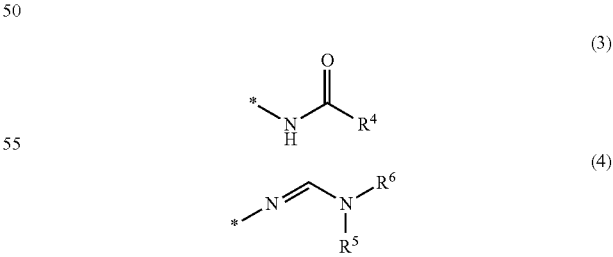

(3)

(4)

wherein * is defined as described above. $R^4$ represents alkyl, arylmethyl or aryloxymethyl.

$R^5$ and $R^6$ are the same or different and each represents alkyl.

$R^3$ represents a hydrogen group which may be protected by trialkyl or diphenylalkylsilyl, or a group represented by the following formula (5).

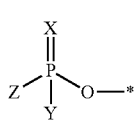

(5)

wherein * is defined as described above.
X represents O or S.
Y represents dialkylamino or alkoxy.
Z represents halogen.

Those which can be exemplified as being encompassed by the present invention are the compound of the invention or a salt thereof.

Hereinafter, the terms used in the present specification are described in detail.

The alkyl can include a straight or branched alkyl having 1 to 8 carbon atoms. Specific examples can include methyl, ethyl, n-propyl, isopropyl, n-butyl, isobutyl, sec-butyl, tert-butyl, n-pentyl, isopentyl, n-hexyl, isohexyl, n-heptyl, iso-heptyl and n-octyl. Among others, an alkyl having 1 to 6 carbon atoms is preferred, and an alkyl having 1 to 3 carbon atoms is more preferred.

The "alkyl" moiety of "trialkylsilyl", "diphenylalkylsilyl", and "dialkylamino" can be exemplified by the same ones as the above "alkyl".

The "aryl" moiety of "arylmethyl", "aryloxymethyl", and "arylsulfonyl" can include an aryl having 6 to 10 carbon atoms. Specific examples can include phenyl, 1-naphthyl and 2-naphthyl. Among others, phenyl is preferred.

The alkoxy can include a straight or branched alkoxy having 1 to 8 carbon atoms such as methoxy, ethoxy, n-propoxy, isopropoxy, n-butyoxy, isobutoxy, sec-butoxy, tert-butoxy, n-pentyloxy, n-hexyloxy, n-heptyloxy, and n-octyloxy.

The halogen can include fluorine, chlorine, bromine and iodine. Among others, chlorine is preferred.

The acyl can include a straight or branched alkanoyl or aroyl. Examples of the alkanoyl can include formyl, acetyl, 2-methylacetyl, 2,2-dimethylacetyl, propionyl, butyryl, isobutyryl, pentanoyl, 2,2-dimethylpropionyl, and hexanoyl. Examples of the aroyl can include benzoyl, toluoyl and naphthoyl. The aroyl may optionally be substituted at substitutable positions and may be substituted with an alkyl(s).

The nucleobase can include adenine, guanine, hypoxanthine, cytosine, thymine, uracil, and modified bases thereof. Examples of such modified nucleobases can include, but are not limited to, pseudouracil, 3-methyluracil, dihydrouracil, 5-alkylcytosines (e.g., 5-methylcytosine), 5-alkyluracils, (e.g., 5-ethyluracil), 5-halouracils (5-bromouracil), 6-azapyrimidine, 6-alkylpyrimidines (6-methyluracil), 2-thiouracil, 4-thiouracil, 4-acetylcycosine, 5-(carboxyhydroxymethyl) uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, $N^6$-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-$N^6$-isopentenyladenine, uracil-5-oxyacetic acid, 2-thiocytosine, purine, 2,6-diaminopurine, 2-aminopurine, isoguanine, indole, imidazole, and xanthine.

Among the compounds of the invention, the following compounds (a) to (c) or salts thereof are preferable.

(a) $N^9$-[(2R,6S)-6-{(tert-butyldimethylsilyloxy)methyl}-4-tritylmorpholin-2-yl]-$N^2$-(phenoxyacetyl)-$O^6$-(2-cyanoethyl)guanine, (b) $N^9$-{(2R,6)-6-hydroxymethyl-4-tritylmorpholin-2-yl}-$N^2$-(phenoxyacetyl)-$O^6$-(2-cyanoethyl)guanine, (c) [(2S,6R)-6-{$N^2$-(phenoxyacetyl)-$O^6$-(2-cyanoethyl)guanin-9-yl}-4-tritylmorpholin-2-yl]methyl dimethylphosphoramidochloridate.

DETAILED DESCRIPTION OF THE INVENTION

Figure 1:
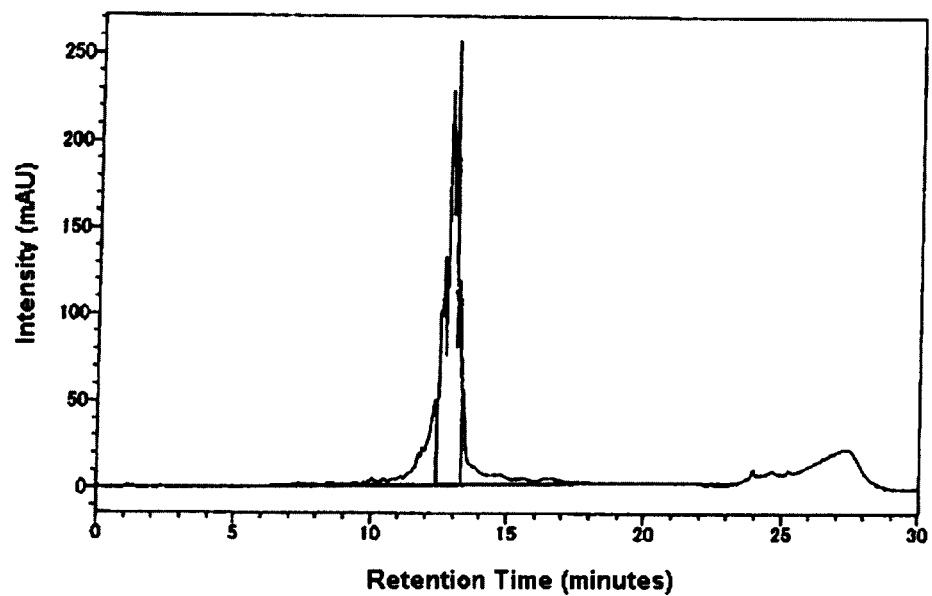
FIG. 1 shows an HPLC chromatographic chart of a crude morpholino nucleic acid oligomer synthesized using a CE-G monomer (for definition, see Table 1). The ordinate represents the intensity (mAU), while the abscissa represents the retention time (minutes).

The embodiments of the present invention are described below.

In the following production method, when a starting material has a substituent influencing the reaction (for example, hydroxy, amino, carboxy), the reaction is usually carried out after preliminary protection of the starting material with a suitable protecting group according to a known method. The protecting group can finally be cleaved according to any known method such as catalytic hydrogenation, alkali treatment, acid treatment and the like.

Production Method of the Compound of the Invention

The compound of the invention can be produced from a known compound or a readily producible intermediate, for example, by Production Method 1 to Production Method 3 shown below.

Production Method 1: When $R^3$ is trialkylsilyloxy or diphenylalkylsilyloxy

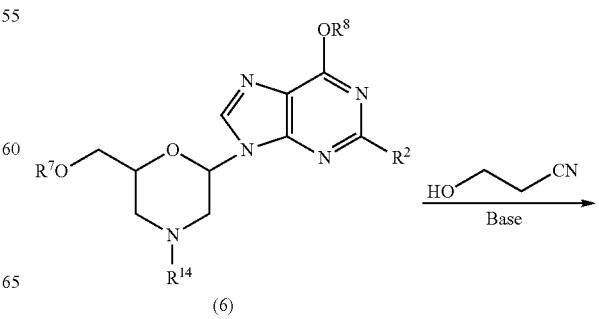

(6)

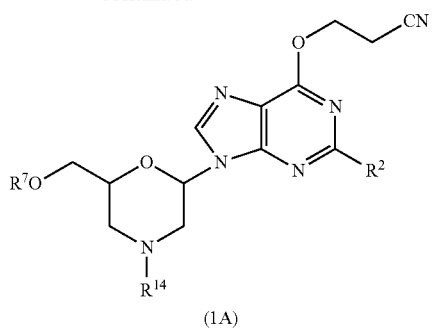

(1A)

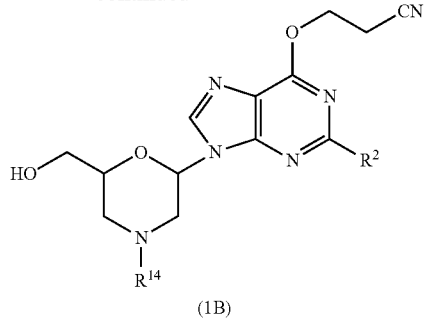

(1B)

wherein $R^2$ is defined as described above.

$R^7$ represents trialkylsilyl or diphenylalkylsilyl.

$R^8$ represents arylsulfonyl which may be substituted with 1 to 3 alkyls.

$R^{14}$ represents the group represented by the aforementioned Formula (2).

This reaction is a condensation reaction of Compound (6) with 2-cyanoethanol, and thus may be carried out according to a method known per se.

The amount of 2-cyanoethanol to be used is suitably within the range from 1 mole to 20 mole for 1 mole of Compound (6), preferably within the range from 1.2 mole to 10 mole for 1 mole of Compound (6). The usable solvent is not limited particularly as long as it is inert to the reaction, and can include, for example, acetonitrile, dichloromethane and N,N-dimethylformamide as well as mixtures thereof. Dichloromethane is especially preferred. The "base" which can be used in this step can include, for example, N-methylpyrrolidine and 1,8-diazabicyclo[5.4.0]undec-7-ene as well as mixtures thereof. The amount of the base to be used is suitably within the range from 1 mole to 20 mole for 1 mole of Compound (6), preferably within the range from 1 mole to 10 mole for 1 mole of Compound (6). The reaction temperature is suitably within the range from 0° C. to 50° C. While the reaction time may vary depending on the kind of the starting material used, the reaction temperature and the like, it is suitably within the range from 1 hour to 30 hours.

Compound (6) as a starting compound can be produced according to the method described in the section for preparing Compound 4 in Example 1 in WO2009/064471.

Production Method 2: When $R^3$ is hydroxyl wherein $R^2$, $R^7$, and $R^{14}$ are defined as described above.

This reaction is a reaction for cleaving $R^7$ on Compound (1A), and thus may be carried out according to a method known per se.

A "reagent for cleaving $R^7$" which can be used in this step can include, for example, tetrabutylammonium fluoride, a salt of an amine with hydrofluoric acid or a mixture of an amine and hydrofluoric acid in a suitable ratio in a suitable solvent.

The usable solvent can include, for example, tetrahydrofuran (THF), acetonitrile, dichloromethane, toluene, dimethyl sulfoxide and N,N-dimethylformamide as well as solvent mixtures thereof. Especially, THF and dichloromethane are preferred.

While the amount of the reagent for cleaving $R^7$ which can be used in this step may vary depending on the kind of Compound (1A), the reagent for cleaving $R^7$ to be used, the solvent to be used and the like, it is suitably within the range from 1 mole to 10 mole for 1 mole of Compound (1A), preferably within the range from 1.2 mole to 5 mole for 1 mole of Compound (A). The reaction temperature is suitably within the range from 0° C. to 50° C. While the reaction time may vary depending on the kind of the starting material, the reaction temperature and the like, it is suitably within the range from 1 hour to 30 hours.

Production Method 3: When $R^3$ is a group represented by the following formula (5)

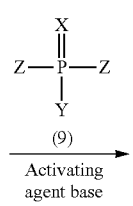

(5)

wherein X, Y, Z, and * are defined as described above.

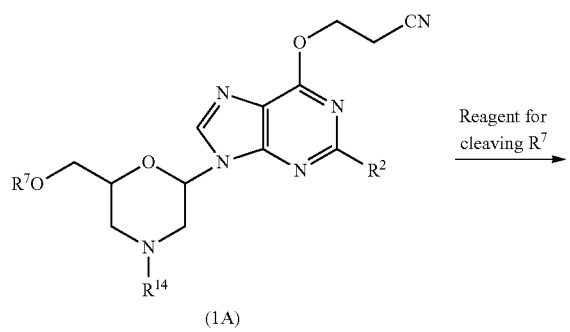

(1A)

Reagent for cleaving $R^7$
→

(1B)

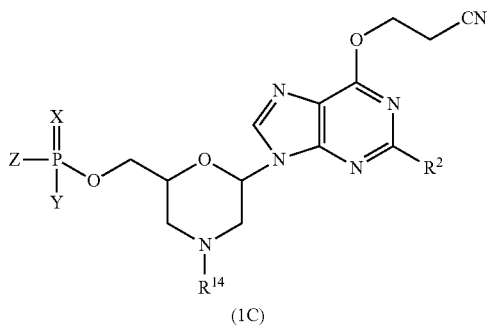

(1C)

wherein $R^2$, $R^{14}$, X, Y, and Z are defined as described above.

This reaction is a phosphoramidating reaction for Compound (1B), and thus may be carried out according to a method known per se.

The usable solvent is not limited particularly as long as it is inert to the reaction, and can include, for example, acetonitrile, dichloromethane and THF.

The amount of Compound (9) which can be used in this step is suitably within the range from 1 mole to 10 mole for 1 mole of Compound (1B), preferably within the range from 1.2 mole to 5 mole for 1 mole of Compound (1B).

The "activating agent" which can be used in this step can include, for example, 1H-tetrazole, 5-ethylthiotetrazole, 4,5-dichloroimidazole, 4,5-dicyanoimidazole, N-methylimidazole, and 4-dimethylaminopyridine. N-Methylimidazole is especially preferred. The amount of the "activating agent" to be used is suitably within the range from 0.2 mole to 3 mole for 1 mole of Compound (9), preferably within the range from 0.5 mole to 2 mole for 1 mole of Compound (9).

The "base" which can be used in this step may, for example, be N-ethylmorpholine. The amount of the base to be used is suitably within the range from 0.8 mole to 5 mole for 1 mole of Compound (9), preferably within the range from 1 mole to 3 mole for 1 mole of Compound (9). The reaction temperature is suitably within the range from 0° C. to 80° C. While the reaction time may vary depending on the kind of the starting material, the reaction temperature and the like, it is suitably in the range from 1 hour to 30 hours.

Production Method 4: When $R^1$ is hydrogen

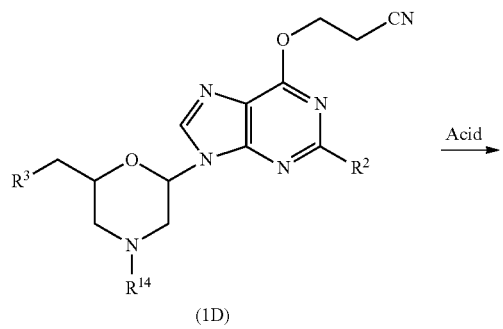

(1D)

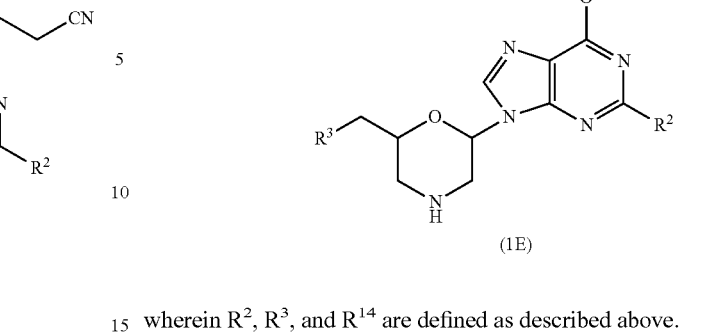

(1E)

wherein $R^2$, $R^3$, and $R^{14}$ are defined as described above.

This reaction is a reaction for deprotecting $R^{14}$ of Compound (1D), and thus may be carried out according to a method known per se.

The "acid" which can be used in this step, i.e., the "reagent for cleaving $R^{14}$" can include, for example, acetic acid, hydrochloric acid or phosphoric acid. The amount of the acid to be used is suitably within the range from 1 mole to 1000 mole for 1 mole of Compound (1D), preferably within the range from 10 mole to 100 mole for 1 mole of Compound (1D).

The solvent to be used is not limited particularly as long as it is inert to the reaction, and can include, for example, dichloromethane, methanol and water.

While the reaction time may vary depending on the kind of the starting material, the reaction temperature and the like, it is suitably within the range from 0.5 hour to 5 hours.

Method for Producing Morpholino Nucleic Acid Oligomer

A preferred morpholino nucleic acid oligomer is an oligomer having a group represented by the following formula as a building block.

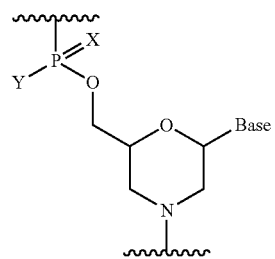

wherein Base represents a nucleic acid base. X and Y are defined as described above.

The morpholino nucleic acid oligomer may be produced, for example, according to the method described in WO1991/009033 or WO2009/064471. Especially, the morpholino nucleic acid oligomer can be produced according to the method described in WO2009/064471, or can be produced according to the method shown below.

As an embodiment of the morpholino nucleic acid oligomer, a compound represented by the following formula (I) (hereinafter referred to an Morpholino nucleic acid oligomer (I)) can be exemplified.

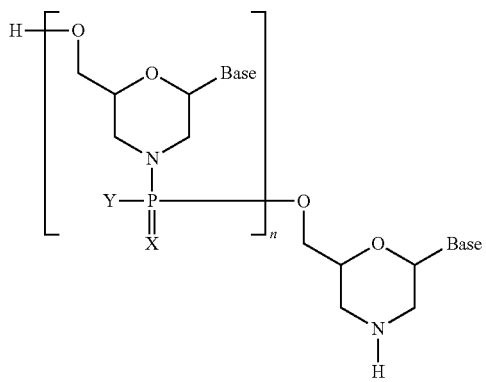

(I)

wherein Base, X, and Y are defined as described above; and n is an integer within the range from 1 to 99, preferably an integer within the range from 18 to 28.

Morpholino nucleic acid oligomer (I) may be produced according to a known method, and may be produced, for example, by carrying out the procedures of the steps described below.

The compounds and the reagents to be used in the steps described below are not limited particularly as long as they are used, generally in producing the morpholino nucleic acid oligomers.

All of the steps described below can be carried out by liquid phase methods or solid phase methods (using manuals or commercially available solid phase automatic synthesizers). When a morpholino nucleic acid oligomer is produced by a solid phase method, a method using an automatic synthesizer is desirable in view of simplification of operational procedures and accuracy of synthesis.

(1) Step A:

A step for producing a compound represented by the following formula (III) (hereinafter referred to as Compound (III)) by allowing an acid to act on a compound represented by the following formula (II) (hereinafter referred to as Compound (II)).

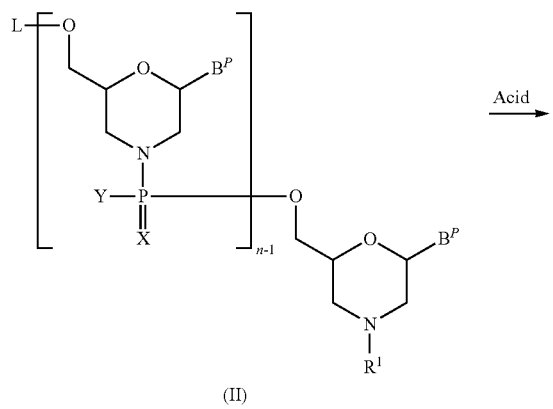

(II)

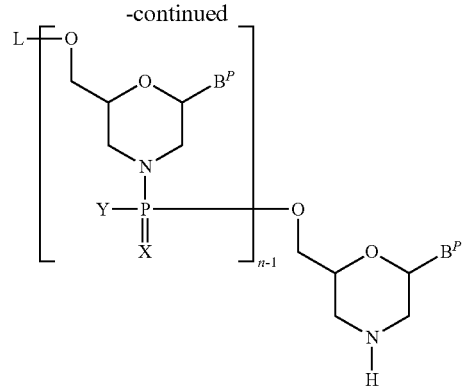

(III)

wherein n, X, and Y are defined as described above;
$B^P$ represents independently a nucleic acid base which may be protected;
$R^1$ represents a trityl group, monomethoxytrityl group or dimethoxytrityl group; and
L represents hydrogen, acyl or a group represented by the following formula (IV) (hereinafter referred to as "Group (IV)").

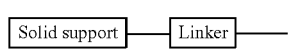

(IV)

The "nucleic acid base" according to $B^P$ can include, for example, a "nucleic acid base" similar to Base. Nevertheless, the amino group or the hydroxy group of the nucleic acid base according to $B^P$ may be protected.

The protecting group for such an amino group is not limited particularly as long as it is used as a protecting group for a nucleic acid, and those exemplified typically can include benzoyl, 4-methoxybenzoyl, acetyl, propionyl, butylyl, isobutylyl, phenylacetyl, phenoxyacetyl, 4-tert-butylphenoxyacetyl, 4-isopropylphenoxyacetyl, and (dimethylamino)methylene. The protecting group for a hydroxy group can include, for example, 2-cyanoethyl, 4-nitrophenethyl, phenylsulfonylethyl, methylsulfonylethyl, trimethylsilylethyl, phenyl which may be substituted in any substitutable positions by 1 to 5 electron-withdrawing groups, diphenylcarbamoyl, dimethylcarbamoyl, diethylcarbamoyl, methylphenylcarbamoyl, 1-pyrrolidinylcarbamoyl, morpholinocarbamoyl, 4-(tert-butylcarboxy)benzyl, 4-[(dimethylamino)carboxy]benzyl, and 4-(phenylcarboxy)benzyl (for example, see WO2009/064471).

Among these, 2-cyanoethyl is preferred as a protecting group for the hydroxy group at the 6-position of the guanine.

The "solid, support" is not limited particularly as long as it can be used in a solid phase reaction of a nucleic acid, and is desirably one which (i) is sparingly soluble in a reagent which can be used in the synthesis of morpholino nucleic acid derivatives (for example, dichloromethane, acetonitrile, tetrazole, N-methylimidamole, pyridine, acetic anhydride, lutidine, trifluoroacetic acid), (ii) is stable chemically to a reagent which can be used in the synthesis of morpholino nucleic acid derivatives, (iii) can be modified chemically, (iv) enables a desired loading of a morpholino nucleic acid derivative, (v) has a strength sufficient to tolerate a high pressure exerted during treatment, (vi) has a constant particle size range and distribution. Those exemplified typically can include swellable polystyrene (for example, aminomethyl polystyrene resin 1% dibenzylbenzene crosslinking (200~400 mesh) (2.4~3.0 mmol/g) (manufactured by Tokyo Chemical Industry Co., Ltd.), Aminomethylated Polystyrene Resin·HCl [dibenzylbenzene 1%, 100~200 mesh] (manufactured by Peptide Institute Inc.)), non-swellable polystyrene (for example, Primer Support (manufactured by GE Healthcare Ltd.)), PEG-chain binding type polystyrene (for example, $NH_2$-PEG resin (manufactured by Watanabe Chemical Industries, Ltd.), TentaGel resin), controlled pore glass (CFG) (for example, CPG's product), oxalylated controlled pore glass (for example, see, Nucleic Acids Research, Vol. 19, 152 (1991) Alul et al.), TentaGel support-aminopolyethylene glycol derivatized support (for example, see, Tetrahedron Letters, Vol. 34, 3373 (1933) Wright et al.), and Poros-polystyrene/divinylbenzene copolymer.

As a "linker", any known one used usually for linking nucleic acids or morpholino nucleic acid derivatives can be used, and can include 3-aminopropyl, succinyl, 2,2-diethanolsulfonyl and a long chain alkylamino (LCAA).

This step can be carried out by allowing an acid to act on Compound (II).

The "acid" which can be used in this step can include, for example, trifluoroacetic acid, dichloroacetic acid and trichloroacetic acid. The amount of the acid to be used is suitably within the range from 0.1 mole to 1000 mole for 1 mole of Compound (II), preferably within the range from 1 mole to 100 mole for 1 mole of Compound (II).

It is also possible to use an organic amine together with the aforementioned acid. The organic amine is not limited particularly and can include, for example, triethylamine. The amount of the organic amine to be used is suitably within the range from 0.01 mole to 10 mole for 1 mole of the acid, preferably within the range from 0.1 mole to 2 mole for 1 mole of the acid.

When using a salt or a mixture of an acid with an organic amine in this step, it can include a salt or a mixture of trifluoroacetic acid with triethylamine, more typically a mixture of 2 equivalents of trifluoroacetic acid with 1 equivalent of triethylamine.

The acid which can be used in this step can be used also as being diluted with a suitable solvent to a concentration within the range from 0.1 to 30%. The solvent is not limited particularly as long as it is inert to the reaction, and can include dichloromethane, acetonitrile, alcohols (ethanol, isopropanol, trifluoroethanol and the like), water, or mixtures thereof.

The reaction temperature of the aforementioned reaction is, for example, preferably within the range from 10° C. to 50° C., more preferably within the range from 20° C. to 40° C., further preferably within the range from 25° C. to 35° C.

While the reaction time may vary depending on the kind of the acid to be used and the reaction temperature, it is suitably within the range from 0.1 minute to 2.4 hours, preferably within the range from 1 minute to 5 hours.

Also after completion of this process, a base may be added if necessary to neutralize the acid remaining in the system. The "base" is not limited particularly and can include for example, diisopropylamine. The base may be used as being diluted with a suitable solvent to a concentration within the range from 0.1% (v/v) to 30% (v/v).

The solvent to be used in this step is not limited particularly as long as it is inert to the reaction, and can include dichloromethane, acetonitrile, alcohols (ethanol, isopropanol, trifluoroethanol and the like), water, or mixtures thereof. The reaction temperature is, for example, preferably within the range from 10° C. to 50° C., more preferably within the range from 20° C. to 40° C., further preferably within the range from 25° C. to 35° C.

While the reaction time may vary depending on the kind of the base and the reaction temperature to be used, it is suitable within the range from 0.1 minute to 24 hours, preferably within the range from 1 minute to 5 hours.

A compound represented by the following formula (IIa) (hereinafter referred to as Compound (IIa)), wherein n is 1 and L is Group (IV) in Compound (II), can be produced according to the method shown below.

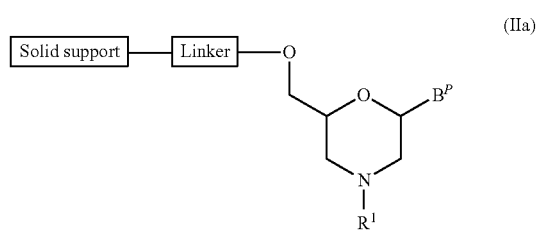

(IIa)

wherein $B^P$, $R^1$, linker, and solid support are defined as described above.

Step 1

A step for producing a compound represented by the following formula (VI) (hereinafter referred to as Compound (VI)) by allowing an acylating agent to act on a compound represented by the following formula (V).

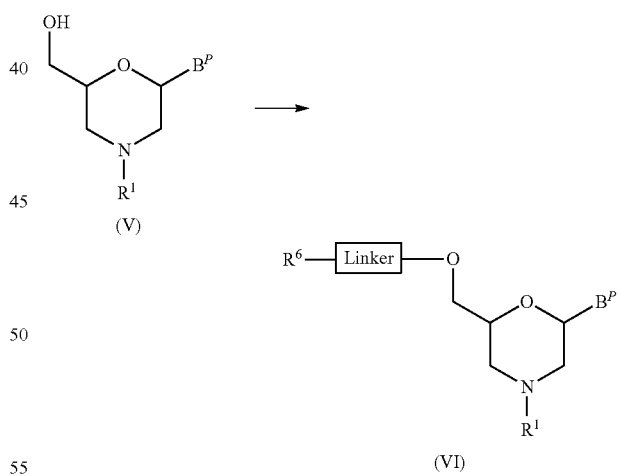

wherein $B^P$, $R^1$, and linker are defined as described above; and $R^6$ represents a hydroxy group, halogen or amino.

This step can be carried out according to a known linker-introducing reaction using Compound (V) as a starting material.

Especially, a compound represented by the following formula (VIa) can be produced according to a method known as an esterification reaction using Compound (V) and succinic anhydride.

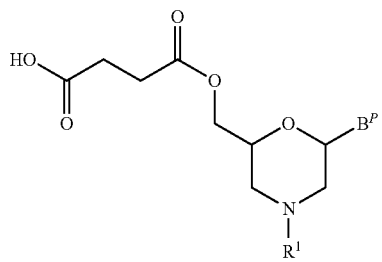

(VIa)

wherein $B^P$, and $R^1$ are defined as described above.

Step 2

A step for producing Compound (IIa) by allowing a condensation agent to act on Compound (VI) and a solid support.

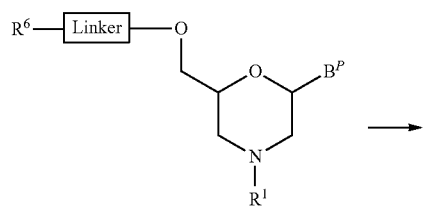

(VI)

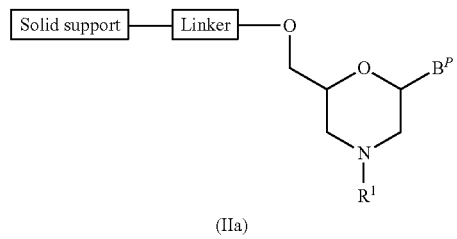

(IIa)

wherein $B^P$, $R^6$, $R^1$, linker, and solid support are defined as described above.

This step is a condensation reaction of Compound (VI) with a solid support and thus may be carried out according to a method known as a condensation reaction.

A compound represented by the following formula (IIa2), wherein n is an integer within the range from 2 to 99 and L is Group (IV) in Compound (II), can be produced by using Compound (IIa) as a starting material, and by repeating the processes of Step A and Step B a desired number of times according to the morpholino nucleic acid oligomer production method described in the present specification.

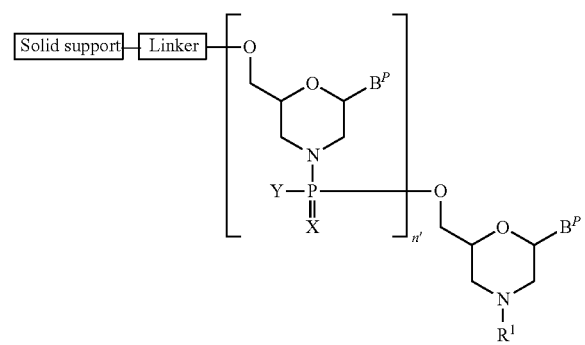

(IIa2)

wherein $B^P$, X, Y, $R^1$, linker, and solid support are defined as described above; and
n' represents an integer in the range from 1 to 98.

A compound represented by the following formula (IIb), wherein n is 1 and L is hydrogen in Compound (II), can be produced for example according to the method described in WO1991/009033.

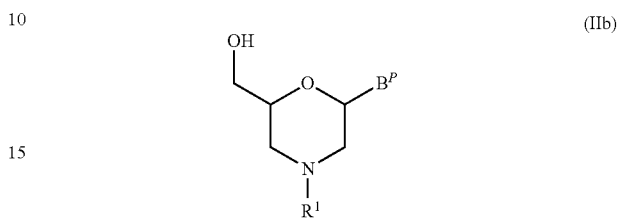

(IIb)

wherein $B^P$ and $R^1$ are defined as described above.

A compound represented by the following formula (IIb2), wherein n is an integer within the range from 2 to 99 and L is hydrogen in Compound (II), can be produced by using Compound (IIb) as a starting material and by repeating the processes of Step A and Step B a desired number of times according to the morpholino nucleic acid oligomer production method described in the present specification.

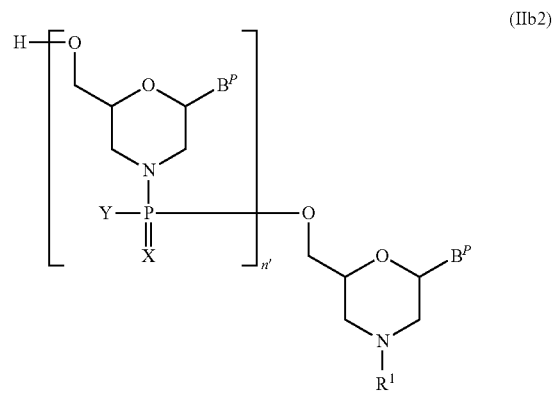

(IIb2)

wherein $B^P$, n', $R^1$, X, and Y are defined as described above.

A compound represented by the following formula (IIc), wherein n=1 and L is acyl in Compound (II), can be produced according to a method known as an acylation reaction to Compound (IIb).

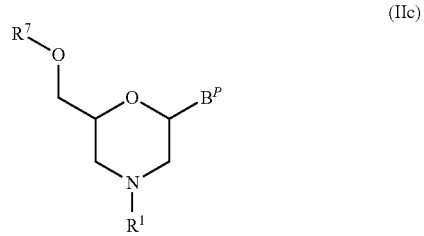

(IIc)

wherein $B^P$ and $R^1$ are defined as described above; and
$R^7$ represents acyl.

A compound represented by the following formula (IIc2), wherein n is an integer within the range from 2 to 99 and L is acyl in Compound (II), can be produced using Compound (IIc) as a starting material and by repeating the processes of Step A and Step B a desired number of times according to the morpholino nucleic acid oligomer production method described in the present specification.

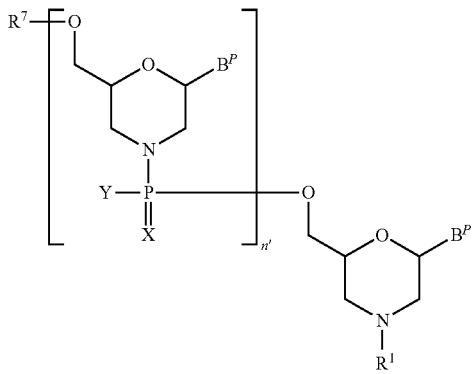

(IIc2)

wherein $B^P$, n', $R^1$, $R^7$, X, and Y are defined as described above.

(2) Step B:

A step for producing a compound represented by the following formula (VII) (hereinafter referred to as Compound (VII)) by allowing a morpholino monomer compound to act on Compound (III) in the presence of a base.

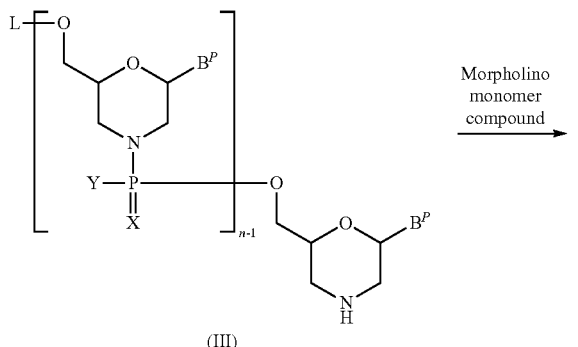

(III)

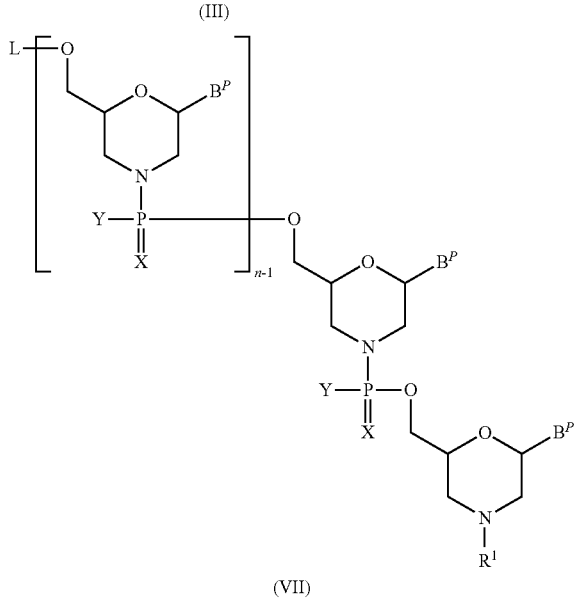

(VII)

wherein $B^P$, L, n, $R^1$, X, and Y are defined as described above.

This step can be carried out by allowing a morpholino monomer compound to act on Compound (III) in the presence of a base.

The morpholino monomer compound can include a compound represented by the following formula (VIII).

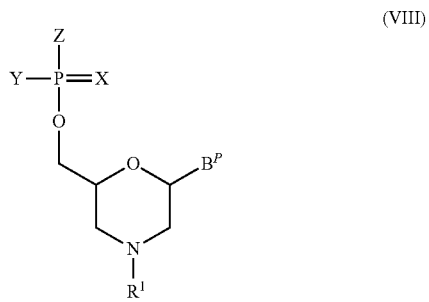

(VIII)

wherein $B^P$, $R^1$, X, Y, and Z are defined as described above.

The "base" which can be used in this step can include diisopropylamine, triethylamine or N-ethylmorpholine. The amount of the base to be used is suitably within the range from 1 mole to 1000 mole for 1 mole of Compound (III), preferably within the range from 10 mole to 100 mole for 1 mole of Compound (III).

The morpholino monomer compound and the base which can foe used in this step can be diluted with suitable solvents to concentrations within the range from 0.1% (v/v) to 30% (v/v). The solvent is not limited particularly as long as it is inert to the reaction, and can include N,N-dimethylimidazolidone, N-methylpiperidone, DMF, dichloromethane, acetonitrile, tetrahydrofuran or a mixture thereof.

The reaction temperature is, for example, preferably within the range from 0° C. to 100° C., more preferably within the range from 10° C. to 50° C.

While the reaction time may vary depending on the kind of the base to be used and the reaction temperature, it is suitably within the range from 1 minute to 48 hours, preferably within the range from 30 minutes to 24 hours.

Also after completion of this process, an acylating agent may be added if necessary. The "acylating agent" can include acetic anhydride, acetyl chloride, and phenoxyacetic anhydride. The acylating agent may be diluted with a suitable solvent to a concentration within the range from 0.1% (v/v) to 30% (v/v). The solvent to be used in this step is not limited particularly as long as it is inert to the reaction, and can include dichloromethane, acetonitrile, alcohols (ethanol, isopropanol, trifluoroethanol and the like), water, or mixtures thereof.

If necessary, it is possible to use, together with the acylating agent, a base such as pyridine, lutidine, collidine, triethylamine, diisopropylethylamine, or N-ethylmorpholine. The amount of the acylating agent to be used is preferably within the range from 0.1 to 10000 mole equivalents, more preferably 1 to 1000 mole equivalents. The amount of the base to be used is suitably within the range from 0.1 mole to 100 mole for 1 mole of the acylating agent, preferably within the range from 2 mole to 10 mole for 1 mole of the acylating agent.

The reaction temperature of this reaction is preferably within the range from 10° C. to 50° C., more preferably within the range from 20° C. to 40° C., further preferably within the range from 25° C. to 35° C. While the reaction time may vary depending on the kind of the acylating agent to be used and the reaction temperature, it is suitably within the range from 0.1 minute to 24 hours, preferably within the range from 1 minute to 5 hours.

(3) Step C:

A step for producing a compound represented by the formula (IX) by allowing a deprotecting agent to act on Compound (VII) produced in Step B, in order to detach the protecting group.

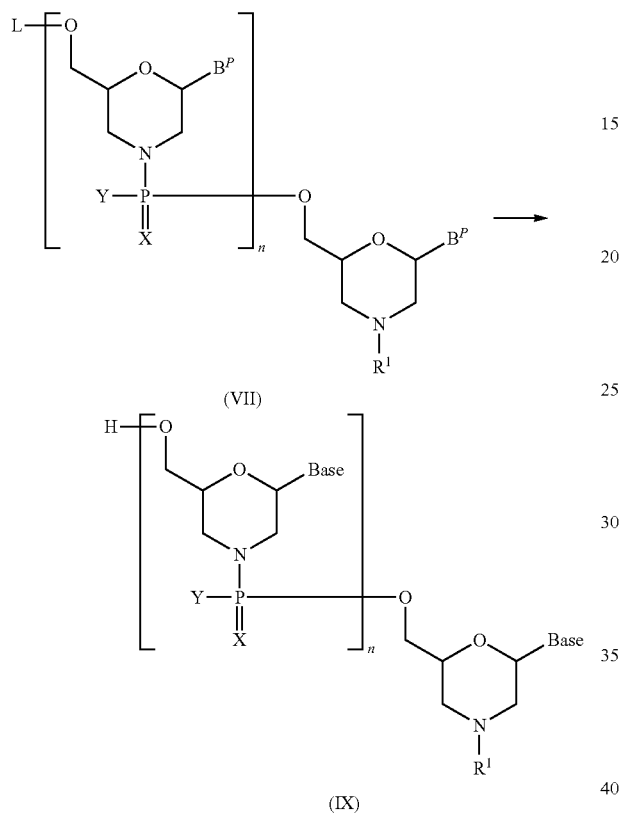

wherein Base, $B^P$, L, n, $R^1$, X, and Y are defined as described above.

This step can be carried out by allowing a deprotecting agent to act on Compound (VII).

The "deprotecting agent" can include a concentrated aqueous ammonium solution and methylamine. The "deprotecting agent" which can be used in this step may be diluted, for example, with water, methanol, ethanol, isopropyl alcohol, acetonitrile, tetrahydrofuran, DMF, N,N-dimethylimidazolidone, N-methylpiperidone or a mixture thereof. Among those, ethanol is preferred. The amount of the deprotecting agent to be used is, for example, suitably within the range from 1 mole to 100000 mole for 1 mole of Compound (VII), preferably within the range from 10 mole to 1000 mole for 1 mole of Compound (VII).

The reaction temperature is, for example, suitably within the range from 15° C. to 75° C., preferably within the range from 40° C. to 70° C., more preferably within the range from 50° C. to 60° C. While the deprotecting reaction time may vary depending on the kind of Compound (VII), the reaction temperature and the like, it is suitably within the range from 10 minutes to 30 hours, preferably within the range from 30 minutes to 24 hours, more preferably within the range from 5 hours to 20 hours.

(4) Step D:

A step for producing a morpholino nucleic acid oligomer (I) by allowing an acid to act on Compound (IX) produced in Step C.

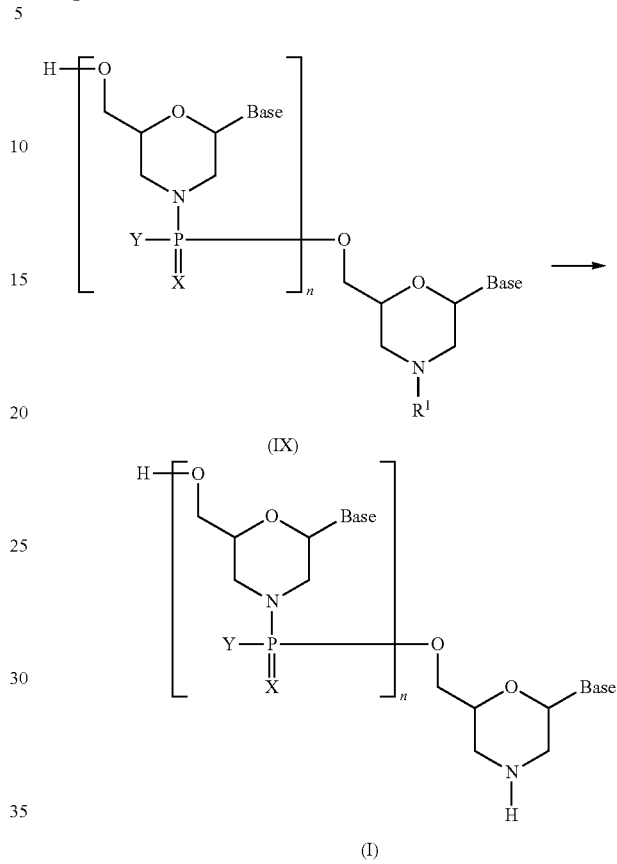

wherein Base, n, $R^1$, X, and Y are defined as described above.

This step can be carried out by adding an acid to Compound (IX).

The "acid" which can be used in this step can include, for example, trichloroacetic acid, dichloroacetic acid, acetic acid, phosphoric acid and hydrochloric acid. The amount of the acid to be used is adjusted suitably to allow the pH of the solution to be within the range from 0.1 to 4.0, more preferably from 1.0 to 3.0. The solvent is not limited particularly as long as it is inert to the reaction, and can include acetonitrile, water or solvent mixtures thereof.

The reaction temperature is preferably within the range from 10° C. to 50° C., more preferably within the range from 20° C. to 40° C., further preferably within the range from 25° C. to 35° C. The deprotecting reaction time may vary depending on the kind of Compound (IX), the reaction temperature and the like, and is suitably within the range from 0.1 minute to 5 hours, preferably within the range from 1 minute to 1 hour, more preferably within the range from 1 minute to 30 minutes.

The morpholino nucleic acid oligomer (I) can be obtained from the reaction mixture obtained in this step by using an ordinary separation and isolation means, such as extraction, concentration, neutralization, filtration, centrifugation, recrystallization, reverse phase column chromatography on $C_8$ to $C_{18}$, cation exchange chromatography, anion exchange chromatography, gel filtration column chromatography, high pressure liquid chromatography, dialysis, and ultrafiltration, which can be carried out alone or in combination. Thereby a desired morpholino nucleic acid oligomer (I) is isolated and purified (for example, see WO1991/09033).

When using a reverse phase chromatography to purify the morpholino nucleic acid oligomer (I), the elution solvent can include a solution mixture of a 20 mM triethylamine/acetic acid buffer solution and acetonitrile.

When using an ion exchange chromatography to purify the morpholino nucleic acid oligomer (I), for example, a solution mixture of a 1 M saline and a 10 mM aqueous solution of sodium hydroxide may be used.

Although the compound of the invention can be used directly as a starting monomer for synthesis of a morpholino nucleic acid oligomer or a starting material for synthesizing such a starting monomer, it can be used in the form of a salt by means of a known method. For example, such a salt may be a salt of a mineral acid such as hydrochloric acid, hydrobromic acid, sulfuric acid, phosphoric acid and the like, and a salt of an organic acid such as acetic acid, citric acid, tartaric acid, maieic acid, succinic acid, tumeric acid, p-toluenesulfonic acid, benzenesulfonic acid, methanesulfonic acid and the like.

Among the compounds of the invention or salts thereof, one having asymmetric carbon atoms may exist, and the respective optical isomers and mixtures thereof are encompassed also by the present invention. The optical isomers can be obtained via optical resolution by a known method using an optically active acid (tartaric acid, dibenzoyltartaric acid, mandelic acid, 10-camphorsulfonic acid and the like) from a racemic form obtained as described above while utilizing the basicity thereof, or can be produced by using a preliminarily prepared optically active compound as a starting material. Otherwise, an optical resolution using a chiral column or an asymmetric synthesis can be used for the production.

Also when geometric isomers or tautomeric isomers of the compound of the invention or a salt thereof exist, the present invention encompasses not only a single isomer thereof but also a mixture thereof.

The compound of the invention or a salt thereof thus produced, can be separated and purified by a technique known per se such as concentration, liquid nature conversion, migration to solvent, solvent extraction, crystallization, recrystallization, fractional distillation, and chromatography.

EXAMPLES

Hereinafter, the present invention will be described in more detail with reference to REFERENCE EXAMPLES, EXAMPLES, PRODUCTION EXAMPLES and TEST EXAMPLES below, but is not deemed to be limited thereto.

Reference Example 1

$N^9$-{(2R,6S)-6-(Hydroxymethyl)morpholin-2-yl}-$N^2$-(phenoxyacetyl) guanine p-toluenesulfone Step 1

Production of $N^2$-(phenoxyacetyl)guanosine

Guanosine, 100 g, was dried at 80° C. under reduced pressure for 24 hours. After 500 mL of pyridine (anhydrous) and 500 mL of dichloromethane (anhydrous) were added thereto, 401 mL of chlorotrimethylsilane was dropwise added to the mixture under an argon atmosphere at 0° C., followed by stirring at room temperature for 3 hours. The mixture was again ice-cooled and 66.3 g of phenoxyacetyl chloride was dropwise added thereto. Under ice cooling, the mixture was stirred further for 3 hours. To the reaction solution was added 500 ml of methanol, and the mixture was stirred at room temperature overnight. The solvent was then removed by distillation under reduced pressure. To the residue was added 500 mL of methanol, and concentration under reduced pressure was performed 3 times. To the residue was added 4 L of water, and the mixture was stirred for an hour under ice cooling. The precipitates formed were taken out by filtration, washed sequentially with water and cold methanol and then dried to give 150.2 g of the objective compound (cf.: Org. Lett. (2004), Vol. 6, No. 15, 2225-2557).

Step 2

$N^9$-{(2R,6S)-6-(Hydroxymethyl)morpholin-2-yl}-$N^2$-(phenoxyacetyl) guanine p-toluenesulfonate In 480 mL of methanol was suspended 30 g of the compound obtained in Step 1, and 130 mL of 2N hydrochloric acid was added to the suspension under ice cooling. Subsequently, 56.8 g of ammonium tetraborate tetrahydrate and 16.2 g of sodium periodate were added to the mixture in the order mentioned and the mixture was stirred at room temperature for 3 hours. The reaction solution was ice cooled and the insoluble matters were removed by filtration, followed by washing with 100 mL of methanol. The filtrate and washing liquid were combined and the mixture was ice cooled. To the mixture was added 11.52 g of 2-picoline borane. After stirring for 20 minutes, 54.6 g of p-toluenesulfonic acid monohydrate was slowly added to the mixture, followed by stirring at 4° C. overnight. The precipitates were taken out by filtration and washed with 500 mL of cold methanol and dried to give 17.7 g of the objective compound (yield: 43.3%).

$^1$H NMR (DMSO-d6): δ 9.9-9.2 (2H, br), 8.35 (1H, s), 7.55 (2H, m), 7.35 (2H, m), 7.10 (2H, d, J=7.82 Hz), 7.00 (3H, m), 5.95 (1H, dd, J=10.64, 2.42 Hz), 4.85 (2H,), 4.00 (1H, m), 3.90-3.60 (2H, m), 3.50-3.20 (5H, m), 2.90 (1H, m), 2.25 (3H, s).

Reference Example 2

Production of 4-{[(2S,6R)-6-(4-benzamido-2-oxopyrimidin-1-yl)-4-tritylmorpholin-2-yl]methoxy}-4-oxobutanoic acid loaded onto aminomethylpolystyrene resin (manufactured by GE Healthcare, Custom Primer Support Amino 200, 28-9229-46)

Under argon atmosphere, 0.46 g of N-{1-[(2R,6S)-6-(hydroxymethyl)-4-tritylmorpholin-2-yl]-2-oxo-1,2-dihydropyrimidin-4-yl}benzamide 0.15 g of 4-dimethylaminopyridine (4-DMAP) were suspended in 10 mL of dichloromethane, and 0.12 g of succinic anhydride was added to the suspension, followed by stirring at room temperature for 3 hours. To the reaction solution was added 1 mL of methanol, and the mixture was concentrated under reduced pressure. The residue was extracted using ethyl acetate and 0.5 M aqueous potassium dihydrogenphosphate solution. The resulting organic layer was washed sequentially with 0.5 M aqueous potassium dihydrogenphosphate solution, water and brine in the order mentioned. The resulting organic layer was dried over sodium sulfate and concentrated under reduced pressure.

After the obtained residue was dissolved in 50 ml of pyridine (dehydrated), 0.1 g of 4-DMAP and 1.5 g of 1-ethyl-3-(3-dimethylaminopropyl)carbodiimide hydrochloride were added to the solution. Then, 5.0 g of Aminomethyl Polystyrene Resin (manufactured by GE Healthcare, Custom Primer Support Amino 200, 28-9229-46) and 1.7 mL of triethylamine were added to the mixture, followed by shaking at room temperature for 6 days. After completion of the reaction, the resin was taken out by filtration. The resulting resin was washed sequentially with pyridine, methanol and dichloromethane in the order mentioned, and dried under reduced pressure. To the resulting resin were added 40 mL of tetrahydrofuran (dehydrate), 3 mL of acetic anhydride and 3 mL of 2,6-lutidine, and the mixture was shaken at room temperature for 1.5 hours. The resin was taken out by filtration, washed sequentially with pyridine, methanol and dichloromethane in the order mentioned, and dried under reduced pressure to give 5.0 g of the product.

The loading amount of the product was determined by the molar amount of the trityl per one g resin by measuring DV absorbance at 409 nm using a known method. The loading amount of the resin was 46.3 μmol/g.

Conditions of UV Measurement
  Device: U-2910 (Hitachi, Ltd.)
  Solvent: methanesulfonic acid
  Wavelength: 265 nm
  ϵ Value: 45000.

Reference Example 3

Production of 4-{[(2S,6R)-6-(4-benzamido-2-oxopyrimidin-1-yl)-4-tritylmorpholin-2-yl]methoxy}-4-oxobutanoic acid loaded onto aminomethyl polystyrene resin cross-linked with 1% DVB (Manufactured by Tokyo Chemical Industry Co., Ltd., A1543)

Under argon atmosphere, 30 g of N-{1-[(2R,6S)-6-(hydroxymethyl)-4-tritylmorpholin-2-yl]-2-oxo-1,2-dihydropyrimidin-4-yl}benzamide and 9.6 g of 4-dimethylaminopyrimidine (4-DMAP) were suspended in 60 mL of dimethylformamide, and 7.86 g of succinic anhydride was added to the suspension, followed by stirring at room temperature for 2 hours. To the reaction solution was added 1 M aqueous potassium dihydrogenphosphate solution, and the mixture was extracted with ethyl acetate. The obtained organic layer was washed sequentially with 1 M aqueous potassium dihydrogenphosphahe solution, water and brine in the order mentioned. The resulting organic layer was dried over magnesium sulfate and concentrated under reduced pressure to give 34.0 g as crude crystal.

After 29.5 g of crude crystal was dissolved in 300 ml of pyridine (dehydrated), 5.1 g of 4-DMAP and 20.1 g of 1-ethyl-3-(3-dimethylaminopropyl)carbodiimide hydrochloride were added to the solution. Then, 25.0 g of Aminomethyl Polystyrene Resin cross-linked with 1% DVB (manufactured by Tokyo Chemical Industry Co., Ltd., A1543) and 24 mL of triethylamine were added to the mixture, followed by shaking at room temperature for 3 days. After completion of the reaction, the resin was taken out by filtration. The resulting resin was washed sequentially with pyridine, methanol and dichloromethane in the order mentioned, and dried under reduced pressure. To the obtained resin were added 300 mL of tetrahydrofuran (dehydrate), 30 mL of acetic anhydride and 30 mL of 2,6-lutidine, and the mixture was shaken at room temperature for 2.5 hours. The resin was taken out by filtration, washed sequentially with pyridine, methanol and dichloromethane in the order mentioned, and dried under reduced pressure to give 33.2 g of the product.

The loading amount of the product was determined by the molar amount of the trityl per one g resin by measuring UV absorbance at 409 nm using a known method. The loading amount of the resin was 292.4 μmol/g.

Conditions of UV Measurement
  Device: U-2910 (Hitachi, Ltd.)
  Solvent: methanesulfonic acid
  Wavelength: 265 nm
  ϵ Value: 45000.

Example 1

[(2S,6R)-6-{$N^2$-(phenoxacetyl)-$O^6$-(2-cyanoethyl)guanin-9-yl}-4-tritylmorpholin-2-yl]methyl dimethylphosphoramidochloridate Step 1

Production of $N^9$-{(2R,6S)-6-hydroxymethyl-4-tritylmorpholin-2-yl}-$N^2$-(phenoxyacetyl)guanine In 30 mL of dichloromethane was suspended 2.0 g of $N^9$-{(2R,6S)-6-(hydroxymethyl)morpholin-2-yl}-$N^2$-(phenoxyacetyl)guanine p-toluenesulfonate (REFERENCE EXAMPLE 1), and 13.9 g of triethylamine and 18.3 g of trityl chloride were added to the suspension under ice cooling. The mixture was stirred at room temperature for an hour. The reaction solution was washed with saturated sodium bicarbonate aqueous solution and then with, water, and dried over sodium sulfate. The organic layer was concentrated under reduced pressure. To the residue was added 40 mL of 0.2 M sodium citrate buffer (pH 3)/methanol (1:4 (v/v)), and the mixture was stirred. Subsequently, 40 mL of water was added and the suspension mixture was stirred for an hour under ice cooling. The precipitates were taken out by filtration, washed with cold methanol and dried to give 1.84 g of the objective compound (yield: 82.0%).

Step 2

Production of $N^9$-[(2R,6S)-6-{(tert-butyldimethylsilyloxy)methyl}-4-tritylmorpholin-2-yl]-$N^2$-(phenoxacetyl)guanine In 300 mL of dichloromethane was dissolved 38.3 g of the compound obtained by Step 1, and 4.64 g of imidazole and 9.47 g of t-butyldimethylsilyl chloride were added to the solution in the order mentioned under ice cooling. The reaction solution was stirred at room temperature for an hour. The reaction solution was washed with 0.2 M sodium citrate buffer (pH 3) and then with brine, and dried over magnesium sulfate. The organic layer was concentrated under reduced pressure to give 44.1 g of the objective compound as a crude product.

Step 3

Production of $N^9$-[(2R,6S)-6-{(tert-butyldimethylsilyloxy)methyl}-5-tritylmorpholin-2-yl]-$N^2$-(phenoxyacetyl)-$O^6$-triisopropylbenzene sulfonyl guanine In 300 mL of dichloromethane was dissolved 44.1 g of the compound obtained by Step 2, and 0.64 g of 4-dimethylaminopyridine, 29.2 mL of triethylamine and 19.0 g of triisopropylbenzenesulfonyl chloride were added to the solution under ice cooling. The reaction solution was stirred at room temperature for an hour. The reaction solution was washed with 1 M aqueous sodium, dihydrogenphosphate solution, and dried, over sodium sulfate. The organic layer was concentrated under reduced pressure to give 60.5 g of the objective compound as a crude product.

Step 4

Production of N⁹-[(2R,6S)-6-{(tert-butyldimethylsilyloxy)methyl}-4-tritylmorpholin-2-yl]-N²-(phenoxyacetyl)-O⁶-(2-cyanoethyl)guanine In 300 mL of dichloromethane was dissolved 60.5 g of the compound obtained by Step 3, and 54.5 mL of N-methylpyrrolidine was added to the solution under ice cooling. The reaction solution was stirred under ice cooling for an hour. Then, 37.2 g of ethylene cyanhydrins, and 11.96 g of 1,8-diazabicyclo[5.4.0]undec-7-ene were added to the solution, and the solution was stirred under ice cooling for 2 hours. The reaction solution was washed with 1 M aqueous sodium dihydrogenphosphate solution and then with water, and dried over sodium sulfate. The organic layer was concentrated under reduced pressure to give 72.4 g of the objective compound as a crude product.

Step 5

Production of N⁹-[(2R,6S)-6-hydroxymethyl-4-tritylmorpholin-2-yl]-N²-(phenoxyacetyl)-O⁶-(2-cyanoethyl)guanine In 300 ml of dichloromethane was dissolved 72.4 g of the compound obtained by Step 4, and 21.1 g of triethylamine trihydrofluoride was added to the solution. The reaction solution was stirred at room temperature for 17 hours. The reaction solution was poured into cold saturated sodium bicarbonate aqueous solution to neutralize the reaction solution, and then the dichloromethane layer was dried over sodium sulfate. The organic layer was concentrated under reduced pressure. The residue was purified by a silica gel column chromatography (PSQ100B (manufactured by FUJI SILYSIA CHEMICAL LTD. The same shall apply hereinafter.)) to give 14.3 g of the objective compound (yield from Step 2: 39.2%).

Step 6

Production of [(2S,6R)-6-{N²-(phenoxyacetyl)-O⁶-(2-cyanoethyl)guanin-9-yl}-4-tritylmorpholin-2-yl] methyl dimethylphosphoramidochloridate Under argon atmosphere, 4.03 mL of dimethylaminophosphoryl dichloride was added to 86 mL of THF, and 3.37 mL of N-methylimidazole was added to the reaction solution. The solution was changed into a suspension. Five minutes later, to the suspension was added 11.86 g of the powdered compound obtained by Step 5. The reaction mixture was stirred for 5 minutes. Then, 2.16 mL of N-ethylmorpholine was added to the mixture, and the solution was stirred at room temperature for 3 hours.
The reaction solution was poured into ice-cooled 1 M sodium dihydrogenphosphate aqueous solution, and was extracted with 300 mL of ethyl acetate. The organic layer was washed with brine and dried over sodium sulfate. The organic layer was concentrated under reduced pressure. The residue was purified by a silica gel column chromatography (PSQ100B) to give 9.9 g of the objective compound (yield: 70.7%).
¹H-NMR (CDCl₃): δ 8.85 (1H, bs), 7.85 (1H, d, J=3.45 Hz), 7.60-7.00 (20H, m), 6.30 (1H, d, J=9.51 Hz), 4.90-4.70 (4H, m), 4.60-4.40 (1H, m), 4.20-4.00 (1H, m), 3.50 (1H, d, J=11.28 Hz), 3.25 (1H, d, J=10.21 Hz), 3.00 (2H, t, J=6.56 Hz), 2.65 (6H, dd, J=13.89, 4.1 Hz), 1.85-1.55 (2H, m).
³¹P-NMR (CDCl₃): δ 20.7097, 20.3500.

Table 1 shows the chemical structures and the abbreviations of the morpholino monomer compounds used in the following PRODUCTION EXAMPLES and TEST EXAMPLES.

TABLE 1

| Abbreviation | Chemical Structure |
|---|---|
| A^P | [structure of morpholino adenine monomer with chlorophosphoramidate, N-benzoyl, trityl] |
| C^P | [structure of morpholino cytosine monomer with chlorophosphoramidate, N-benzoyl, trityl] |
| T^P | [structure of morpholino thymine monomer with chlorophosphoramidate, trityl] |

TABLE 1-continued

| Abbreviation | Chemical Structure |
|---|---|
| CE-G | 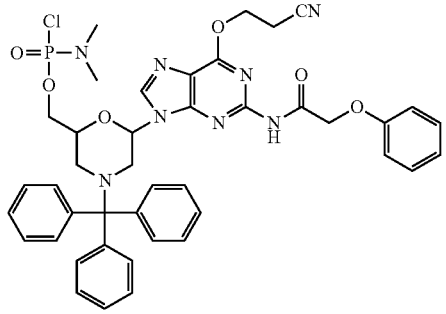 [SMILES: CN(C)P(=O)(Cl)OCC1CN(C(c2ccccc2)(c2ccccc2)c2ccccc2)CC(n2cnc3c(OCCC#N)nc(NC(=O)COc4ccccc4)nc32)O1] |
| POB-G | 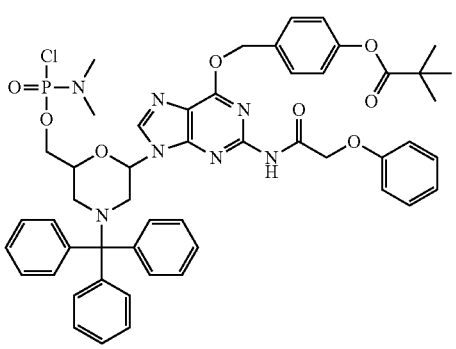 [SMILES: CN(C)P(=O)(Cl)OCC1CN(C(c2ccccc2)(c2ccccc2)c2ccccc2)CC(n2cnc3c(OCc4ccc(OC(=O)C(C)(C)C)cc4)nc(NC(=O)COc4ccccc4)nc32)O1] |

Production Example 1

Synthesis of Morpholino Nucleic Acid Oligomer Having the Following Structure and Base Sequence 5'-CAGTGC-3' Using CE-G

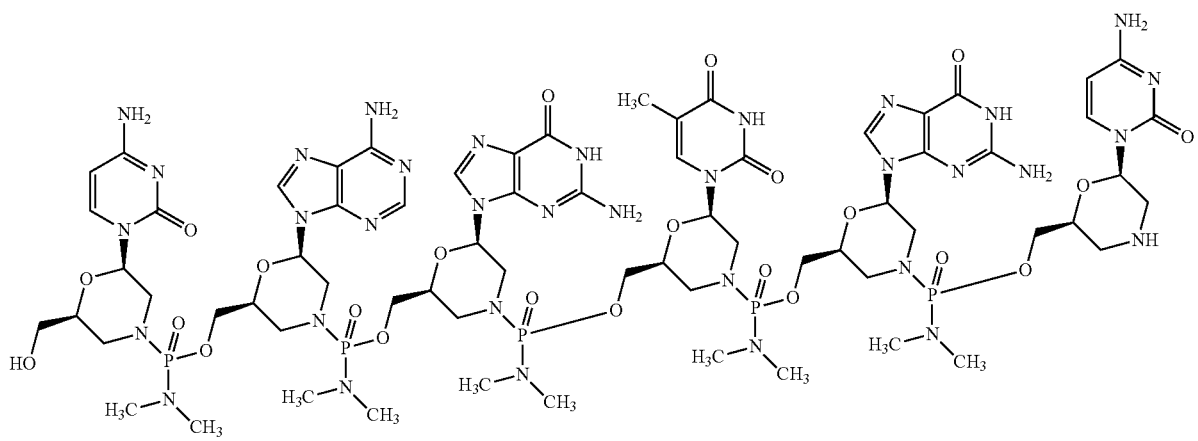 [SMILES: Cc1cn([C@H]2CN(P(=O)(OC[C@@H]3CN(P(=O)(OC[C@@H]4CNC[C@H](n5ccc(N)nc5=O)O4)N(C)C)C[C@H](n4cnc5c(=O)[nH]c(N)nc54)O3)N(C)C)C[C@@H](COP(=O)(N(C)C)N3C[C@@H](COP(=O)(N(C)C)N4C[C@@H](COP(=O)(N(C)C)N5C[C@@H](CO)O[C@@H](n6ccc(N)nc6=O)C5)O[C@@H](n5cnc6c(N)ncnc65)C4)O[C@@H](n4cnc5c(=O)[nH]c(N)nc54)C3)O2)c(=O)[nH]c1=O]

Step 1

216 mg (10 μmol) of 4-{[(2S,6R)-6-(4-benzamide-2-oxypyrimidin-1-yl)-4-tritylmorpholin-2-yl]methoxy}-4-oxobutanoic acid supported on an aminomethylpolystyrene resin (Reference Example 2) was transferred into a column for synthesis, which was loaded in an automatic synthesizing machine (Oligopilot 10: manufactured by GE Healthcare). Other required reagents were prepared and also loaded. The solid phase synthesis was performed at 50° C. (using a column oven) under the condition shown in Table 2.

TABLE 2

| Step | Process | Solution | Time (min.) |
|---|---|---|---|
| 1 | Deblocking | Deblocking solution | 2.0 |
| 2 | Washing | Acetonitrile | 1.0 |
| 3 | Coupling | Morpholino monomer solution (7 eq.) + Activator solution (*) | 90 |
| 4 | Washing | Acetonitrile | 1.0 |

(*) The monomer solution and the activator solution were set at a volume ratio of 6:4.

As a deblocking solution, a dichloromethane solution containing 3% (w/v) trichloroacetic acid was used. As an activator, an acetonitrile solution containing 20% (v/v) N,N-diisopropylethylamine and 10% (v/v) tetrahydrofuran was used. As morpholino monomer compounds, $A^P$, $C^P$, $T^P$ and CE-G shown in Table 1 were used.

As a morpholino monomer solution, the aforementioned morpholino monomer compound dissolved at 0.13 to 0.15 M in tetrahydrofuran was used ($A^P$, $C^P$: 0.14 M; $T^P$: 0.15 M; CE-G: 0.13 M).

Step 2

The morpholino nucleic acid oligomer supported on the aminomethylpolystyrene resin obtained in Step 1 was taken out of the reaction vessel, and dried under reduced pressure at room temperature for 2 hours or longer. 10 mg of the morpholino nucleic acid oligomer supported on the aminomethylpolystyrene resin thus dried was placed in the reaction vessel, to which 1 mL of 28% aqueous ammonia/ethanol (1/3) was added and stirred for 15 hours at 55° C. The aminomethylpolystyrene resin was filtered and washed with 1.0 mL of ethanol. The filtrate obtained was combined with 10 mL of ethyl ether. After centrifugation, the supernatant was discarded, and then after drying under reduced pressure, the intended substance was obtained as a white precipitate.

MALDI-TOF-MS: Calculated: 1921.66
Found: 1917.69.

Production Example 2

Synthesis of Morpholino Nucleic Acid Oligomer Having Base Sequence 5'-CAGTGC-3' Using POB-G Instead of CE-G monomer, [(2S,6R)-6-{$N^2$-(phenoxyacetyl)-$O^6$-(pivaloyloxybenzyl)guanin-9-yl}-4-tritylmorpholin-2-yl]methyl dimethylphosphoramidochloridate (see, WO2009/064471 A1, hereinafter referred to as POB-G (see Table 1)) was used, and the morpholino nucleic acid oligomer having the sequence similar to that in Production Example 1 was produced by the methods similar to that in Step 1 and Step 2 in Production Example 1.

Production Example 3

Synthesis of Morpholino Nucleic Acid Oligomer Having Base Sequence 5'-CCTCCGGTTCTGAAGGTGTT-3'

6.02 g (1.75 mmol) of 4-{[(2S,6R)-6-(4-benzamide-2-oxopyrimidin-1-yl)-4-tritylmorpholin-2-yl]methoxy}-4-oxobutanoic acid supported on an aminomethylpolystyrene resin (Reference Example 3) was transferred into a reaction vessel, and the vessel was added with 90 mL of dichloromethane, and allowed to stand for 30 minutes. After filtration, the synthetic cycle shown in Table 3 was started. In order to obtain the compound having the designated base sequence, the morpholino monomer compounds in the respective cycles were added as appropriate.

TABLE 3

| Step | Reagent | Volume (mL) | Time (min) |
|---|---|---|---|
| 1 | deblocking solution | 90 | 5.0 |
| 2 | deblocking solution | 90 | 5.0 |
| 3 | deblocking solution | 90 | 5.0 |
| 4 | deblocking solution | 90 | 2.0 |
| 5 | deblocking solution | 90 | 5.0 |
| 6 | deblocking solution | 90 | 5.0 |
| 7 | neutralizing solution | 90 | 1.5 |
| 8 | neutralizing solution | 90 | 1.5 |
| 9 | neutralizing solution | 90 | 1.5 |
| 10 | neutralizing solution | 90 | 1.5 |
| 11 | neutralizing solution | 90 | 1.5 |
| 12 | neutralizing solution | 90 | 1.5 |
| 13 | dichloromethane | 90 | 0.5 |
| 14 | dichloromethane | 90 | 0.5 |
| 15 | dichloromethane | 90 | 0.5 |
| 16 | coupling solution B | 60 | 0.5 |
| 17 | coupling solution A | 20-35 *1 | 90-300 *2 |
| 18 | dichloromethane | 90 | 0.5 |
| 19 | dichloromethane | 90 | 0.5 |
| 20 | dichloromethane | 90 | 0.5 |
| 21 | capping solution | 90 | 3.0 |
| 22 | capping solution | 90 | 3.0 |
| 23 | dichloromethane | 90 | 0.5 |
| 24 | dichloromethane | 90 | 0.5 |
| 25 | dichloromethane | 90 | 0.5 |

*1 Minimum amount required for allowing solid support to be swollen to enable stirring.
*2 90 minutes for 10-mer or under, 300 minutes for 11- to 21-mers.

As a deblocking solution, a mixture of trifluoroacetic acid (2 equivalents) and triethylamine (1 equivalent) dissolved at 3% (w/v) in a dichloromethane solution containing 1% (w/v) ethanol and 10% (v/v) 2,2,2-trifluoroethanol was used. As a neutralizing solution, N,N-diisopropylethylamine dissolved at 5% (v/v) in a dichloromethane solution containing 25% (v/v) 2-propanol was used.

As Coupling Solution A, a morpholino monomer compound ($A^P$, $C^P$, $T^P$ and CE-G) dissolved at 0.15 M in 1,3-dimethyl-2-imidazolidinone solution containing 10% (v/v) N,N-diisopropylethylamine was used. As Coupling Solution B, N,N-diisopropylethylamine dissolved at 10% (v/v) in 1,3-dimethyl-2-imidazolidinone was used. As Capping Solution, dichloromethane containing 20% (v/v) acetic anhydride and 30% (v/v) 2,6-lutidine dissolved therein was used.

The morpholino nucleic acid oligomer supported on the aminomethylpolystyrene resin synthesized as described above was recovered from the reaction vessel, and dried under reduced pressure at room temperature for 2 hours or longer. The morpholino nucleic acid oligomer supported on the aminomethylpolystyrene resin thus dried was placed in the reaction vessel, to which 350 mL of 28% aqueous ammonia/ethanol (1/4) was added and stirred for 15 hours at 55° C. The aminomethylpolystyrene resin was filtered and washed with 150 mL of water/ethanol (1/4). The filtrate obtained was concentrated under reduced pressure. The residue obtained was dissolved in 400 ml of a solvent mixture of 20 mM acetic acid-triethylamine buffer (TEAA buffer) and acetonitrile (4/1) and filtered through a membrane filter. The filtrate obtained was purified by a reverse phase HPLC. The conditions used are shown in Table 4.

TABLE 4

| Column | XTerra MS18 (Waters, φ50 × 100 mm, 1CV = 200 mL) |
|---|---|
| Flow rate | 60 mL/min |
| Column temperature | room temperature |
| Solution A | 20 mM TEAA buffer |
| Solution B | $CH_3CN$ |
| Gradient | (B) conc. 20→50%/9CV |

Each fraction was analysed and the intended substance was recovered and concentrated under reduced pressure to obtain a pale yellow solid. The solid obtained was suspended in 200 mL of a 10 mM aqueous solution of phosphoric acid. The suspension was added with 10 mL of a 2 M aqueous solution of phosphoric acid and stirred for 15 minutes. Then, 15 mL of a 2 M aqueous solution of sodium hydroxide was also added for neutralization. And then, 20 mL of the 2 M aqueous solution of sodium hydroxide was further added to basify the solution. The mixture was then filtered through a membrane filter (0.22 μm) and rinsed with 180 mL of a 10 mM aqueous solution of sodium hydroxide to obtain an aqueous solution (400 mL) containing the intended substance (5.8 g, yield: 50%).

ESI-TOF-MS Calculated: 6609.62
Found: 6609.09.

Test Example 1

Comparison of Morpholino Nucleic Acid Oligomer Produced Using the Compound of the Invention (CE-G) (Production Example 1) and Morpholino Nucleic Oligomer Produced Using Prior Art Compound (POB-G) (Production Example 2)

(1) Comparison of Purity of Yield of Synthesized Morpholino Nucleic Acid Oligomers Each of the morpholino nucleic acid oligomers supported on the aminoethylpolystyrene resins obtained by the procedures similar to Step 1 in Production Example 1 and Step 1 in Production Example 2 was treated with a concentrated aqueous ammonia/ethanol mixture solution and the morpholino nucleic acid oligomers were cleaved from the solid phase supports. After removing the solid support by filtration, the filtrate was added with a large excess of ether and subjected to centrifugation, and the supernatant was discarded to recover the crude product of the relevant oligomer as a solid. The solid was dried and then dissolved in water (20 mL), 5 µl of which was taken and subjected to HPLC to measure the designated morpholino nucleic acid oligomer content in the relevant crude mixture. The results are shown in HPLC chromatograms respectively in FIG. 1 and FIG. 2.

Figure 2:
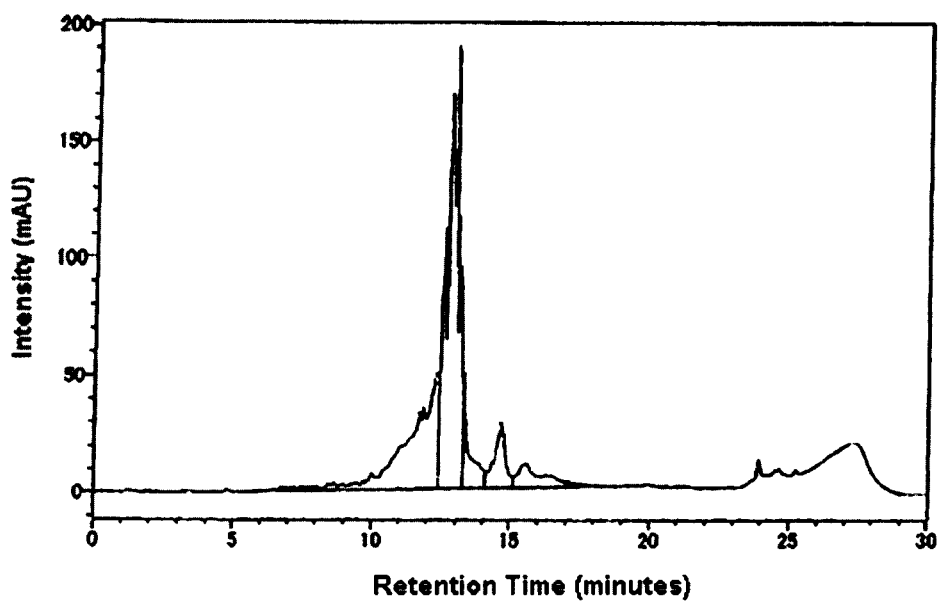
FIG. 2 shows an HPLC chromatographic chart of a crude morpholino nucleic acid oligomer synthesized using a POB-G monomer (for definition, see Table 1). The ordinate represents the intensity (mAU), while the abscissa represents the retention time (minutes).

The measurement conditions are shown below.
Measurement Conditions:
HPLC Instrument
  Pumping unit: LC-10AT VP (produced by Shimadzu Corporation)
  Detector: SPD-10AVP (produced Shimadzu Corporation)
Reverse Phase HPLC Column
  XBridge [2.5 µm, φ4.6 mm×50 mm] (produced by Waters)
  Column temperature: 60° C.
Mobile Phase
  Gradient: Linear gradient 20 minutes (Solution B: 0 to 40%)
  Solution A: 50 mM triethylamino—acetic acid buffer solution
  Solution B: Acetonitrile
Mobile phase flow rate: 0.75 ml/min
UV/Visible spectrophotometer detection wavelength: 260 nm The area percent (%) and the peak area (µUA·sec) of the designated morpholino nucleic acid oligomer contained in the crude mixture obtained by analyzing the HPLC chromatograms in FIG. 1 and FIG. 2 are shown in Table 5.

TABLE 5

| | Type of G-monomer | Area percent (%) | Peak area (µAU · sec) |
|---|---|---|---|
| PRODUCTION EXAMPLE 1 | CE-G | 67.0 | 6868358 |
| PRODUCTION EXAMPLE 2 | POB-G | 47.8 | 5364747 |

The results shown in Table 5 indicate that the area percent is higher and the peak area is larger when using the CE-G monomer in the synthesis of the morpholino nucleic acid oligomers than when using the POB-G monomer. The morpholino nucleic acid oligomer synthesized using the compound of the invention has a higher purity and yield. It is clear that the present invention is superior to the prior art.
(2) Comparison of Synthesized Morpholino Nucleic Acid Oligomers by MS Analysis The respective crude morpholino nucleic acid oligomers obtained in Section (1) described above wore examined for the mass spectra (MALDI-TOF-MS; produced by Autoflex/Bruker Daltonics) to obtain the mass spectrum shown respectively in FIG. 3 and FIG. 4.

Figure 3:
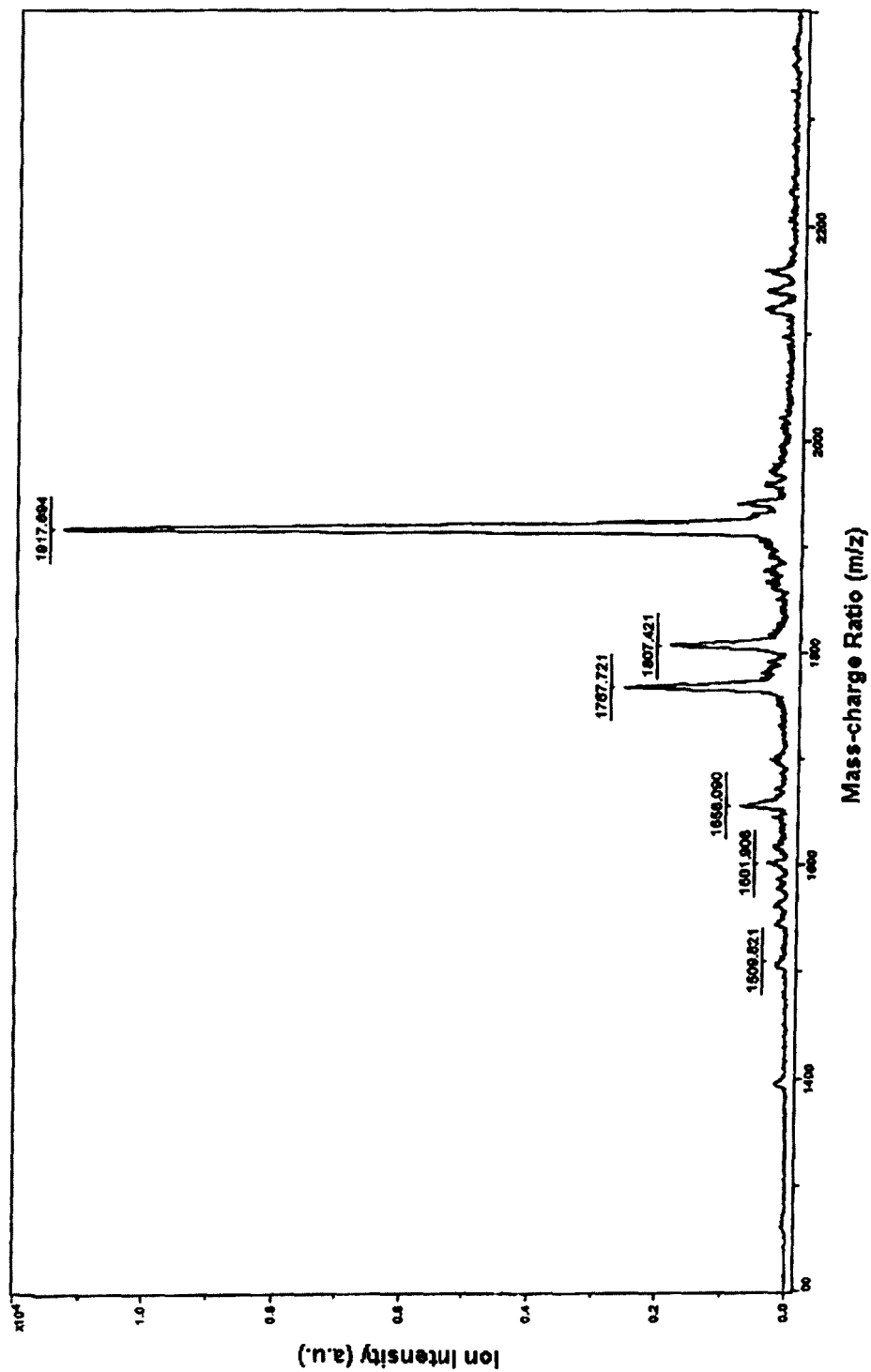
FIG. 3 shows an MS spectral chart of a crude morpholino nucleic acid oligomer synthesized using a CE-G monomer. The ordinate represents the ion intensity (a.u.), while the abscissa represents the mass-charge ratio (m/z).
Figure 4:
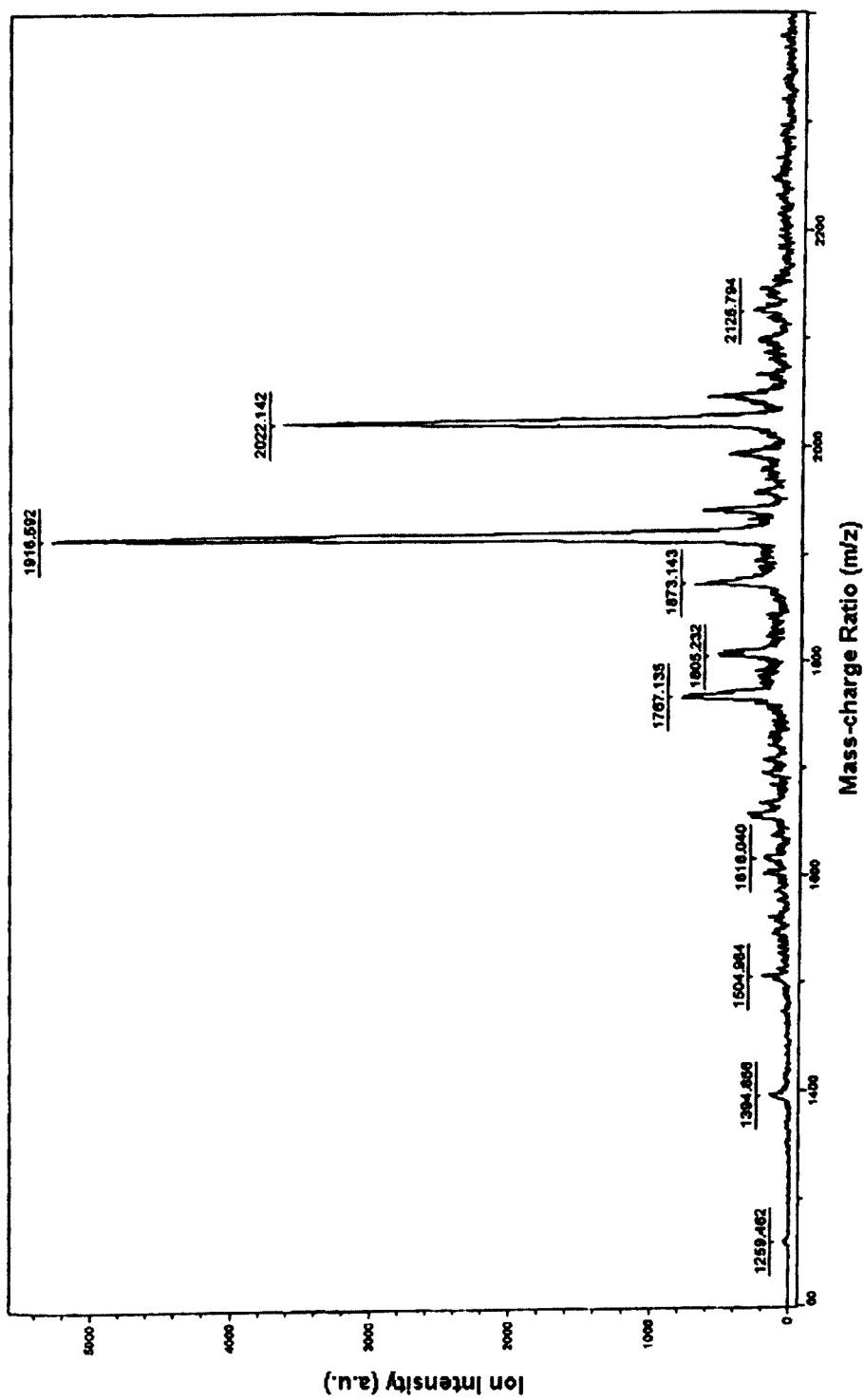
FIG. 4 shows an MS spectral chart of a crude morpholino nucleic acid oligomer synthesized using a POB-G monomer. The ordinate represents the ion intensity (a.u.) and the abscissa represents the mass-charge ratio (m/z).

As a result, it was revealed that when using the POB-G monomer (FIG. 4) there was observed a by-product which was not observed when using the CE-G monomer (FIG. 3). The measured value of the molecular weight of this by-product was greater by 106 than the standard peak of the designated morpholino nucleic acid oligomer, suggesting the presence of a p-hydroxybenzyl adduce which was reported in WO2009/064471.

On the other hand, when using the CE-G monomer, the acrylonitrile adduct was not found in spite of the β-cleavage of the CE group (FIG. 3), indicating that the CE-G monomer performs excellently in the synthesis of the morpholino nucleic acid oligomer.

The invention claimed is:
1. A compound represented by the following general formula (1) or a salt thereof:

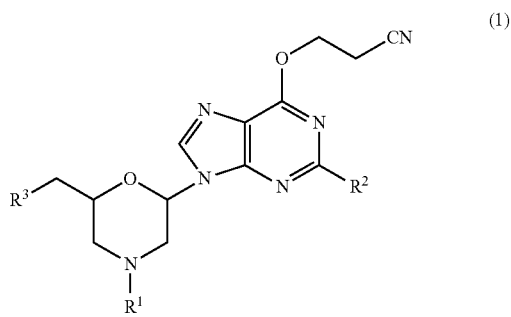

wherein
  $R^1$ represents hydrogen or a group represented by the following general formula (2)

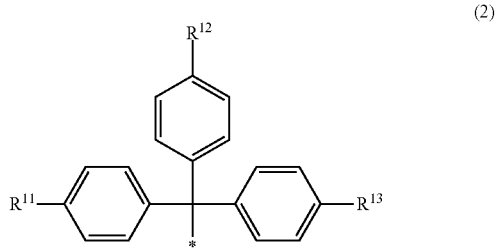

wherein * represents the binding position, and $R^{11}$, $R^{12}$, $R^{13}$ are the same or different and each represents hydrogen, alkyl or alkoxy;
  $R^2$ represents a group represented by the following general formula (3) or (4)

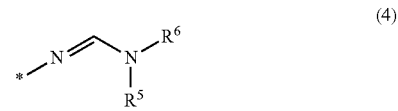

wherein *is defined as described above, $R^4$ represents alkyl, arylmethyl or aryloxymethyl, and $R^5$, $R^6$ are the same or different and each represents alkyl; and
  $R^3$ represents a hydroxy group which may be protected by trialkylsilyl or diphenylalkylsilyl, or a group represented by the following general formula (5)

wherein * is defined as described above, X represents O or S, Y represents dialkylamino or alkoxy, and Z represents halogen.

2. The compound or salt thereof according to claim 1, wherein X is O, Y is dialkylamino, and Z is chlorine.

3. The compound or salt thereof according to claim 1, wherein $R^3$ is a hydroxy group which may be protected by t-butyldimethylsilyl or t-butyldiphenylsilyl.

4. The compound or salt thereof according to claim 1, wherein $R^4$ is phenoxymethyl.

5. The compound or salt thereof according to claim 1, wherein $R^1$ is trityl, 4-methoxytrityl, 4-methyltrityl, 4,4'-dimethylrityl, 4,4'-dimethoxytrityl, or 4,4',4"-trimethyltrityl.

6. A compound selected from the group consisting of the following compounds:
   $N^9$-[(2R,6S)-6-{(tert-butyldimethylsilyloxy)methyl}-4-tritylmorpholin-2-yl]-$N^2$-(phenoxyacetyl)-$O^6$-(2-cyanoethyl)guanine,
   $N^9$-{(2R,6S)-6-hydroxymethyl-4-tritylmorpholin-2-yl}-$N^2$-(phenoxyacetyl)-$O^6$-(2-cyanoethyl)guanine, and
   [(2S,6R)-6-{$N^2$-(phenoxyacetyl)-$O^6$-(2-cyanoethyl)guanin-9-yl}-4-tritylmorpholin-2-yl]methyl dimethylphosporamidochloridate;
   or a salt thereof.

7. A method of increasing the chain length of as mopholino nucleic acid oligomer, the method comprising the steps of:
   providing a compound represented by the following general formula (1) or a salt thereof;

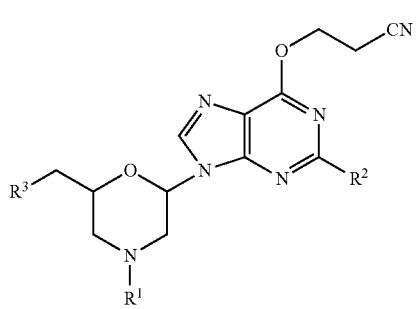

(1)

and
   reacting the compound or salt thereof with the morpholino nucleic acid oligomer;
wherein:
   $R^1$ represents hydrogen or a group represented by the following general formula (2)

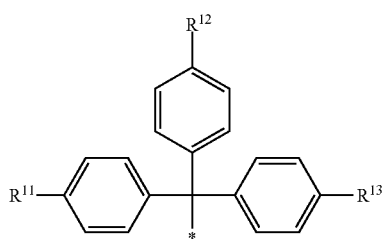

(2)

wherein * represents the binding position, and $R^{11}$, $R^{12}$, $R^{13}$ are the same or different and each represents hydrogen, alkyl or alkoxy;
   $R^2$ represents a group represented by the following general formula (3) or (4)

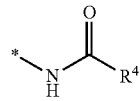

(3)

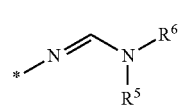

(4)

wherein * is defined as described above, $R^4$ represents alkyl, arylmethy or aryloxymethyl, and $R^5$, $R^6$ are the same or different and each represents alkyl; and
   $R^3$ represents a group represented by the following general formula (5)

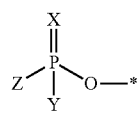

(5)

wherein * is defined as described above, X represents O or S, Y represents dialkylamino or alkoxy, and Z represents halogen.

8. The method according to claim 7, wherein the reaction step is performed with the morpholino nucleic acid oligomer attached to a solid support.

9. The method according to claim 7, wherein X is O, Y is dialkylamino, and Z is chlorine.

10. The method according to claim 9, wherein the reaction step is performed with the morpholino nucleic acid oligomer attached to a solid support.

11. The method according to claim 7, wherein $R^2$ is the group represented by the general formula (3), and $R^4$ is phenoxymethyl.

12. The method according to claim 11, wherein the reaction step is performed with the morpholino nucleic acid oligomer attached to a solid support.

13. The method according to claim 7, wherein $R^1$ is trityl, 4-methoxytrityl, 4-methyltrityl, 4,4'-dimethytrityl, 4,4'-dimethoxytrityl, or 4,4',4"-trimethyltrityl.

14. The method according to claim 13, wherein the reaction step is performed with the morpholino nucleic acid oligomer attached to a solid support.

15. The method according to claim 7, wherein the compound or salt thereof is [(2S,6R)-6-{$N^2$-(phenoxyacetyl)-$O^6$-(2-cyanoethyl)guanin-9-yl}-4-tritylmorpholin-2-yl]methyl dimethylphosphoramidochloridate or a salt thereof.

16. The method according to claim 15, wherein the reaction step is performed with the morpholino nucleic acid oligomer attached to a solid support.

* * * * *